United States Patent
Kawahara

(10) Patent No.: US 9,334,510 B2
(45) Date of Patent: May 10, 2016

(54) METHOD OF PRODUCING LIPIDS USING A THIOESTERASE VARIANT

(71) Applicant: Kao Corporation, Chuo-ku, Tokyo (JP)

(72) Inventor: Akihito Kawahara, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/426,801

(22) PCT Filed: Aug. 22, 2013

(86) PCT No.: PCT/JP2013/072418
§ 371 (c)(1),
(2) Date: Mar. 9, 2015

(87) PCT Pub. No.: WO2014/045793
PCT Pub. Date: Mar. 27, 2014

(65) Prior Publication Data
US 2015/0247173 A1    Sep. 3, 2015

(30) Foreign Application Priority Data
Sep. 20, 2012 (JP) .................. 2012-206972

(51) Int. Cl.
*C12P 7/64* (2006.01)
*C12N 9/16* (2006.01)

(52) U.S. Cl.
CPC ............ *C12P 7/6409* (2013.01); *C12N 9/16* (2013.01); *C12Y 301/02014* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,925,805 A | 7/1999 | Ohlrogge et al. | |
| 2004/0093638 A1 | 5/2004 | Sasaki et al. | |
| 2013/0029387 A1 | 1/2013 | Nikolau et al. | |
| 2013/0059351 A1 | 3/2013 | Tojo et al. | |
| 2013/0219557 A1 | 8/2013 | Tojo et al. | |

FOREIGN PATENT DOCUMENTS

| | | |
|---|---|---|
| JP | 08-205863 A | 8/1996 |
| JP | 11-506323 A | 6/1999 |
| JP | 2002-335786 A | 11/2002 |
| WO | WO 96/38573 A1 | 12/1996 |
| WO | WO 98/55633 A1 | 12/1998 |
| WO | WO 00/36114 A1 | 6/2000 |
| WO | WO 2008/076377 A2 | 6/2008 |
| WO | WO 2011/077931 A1 | 6/2011 |
| WO | WO 2011/138891 A1 | 11/2011 |

OTHER PUBLICATIONS

International Search Report (ISR) for PCT/JP2013/072418; I.A. fd: Aug. 22, 2013, mailed Sep. 24, 2013, the Japanese Patent Office, Tokyo, Japan.
International Preliminary Report on Patentability (IPRP) including the Written Opinion of the International Searching Authority (PCT Rule 44*bis*) for PCT/JP2013/072418; I.A. fd: Aug. 22, 2013, issued Mar. 24, 2015, by the International Bureau of WIPO, Geneva, Switzerland.
Tojo, T. et al., "Characterization of acyl-ACP thioesterase derived from coconut," ("Kokoyashi Yurai Acyl-ACP Thioesterase wa Chusa Shibosan no Seisan ni Kan'yo suru"), Japan Society for Bioscience, Biotechnology, and Agrochemistry, Taikai Koen Yoshishu, Mar. 5, 2012, Abstract 2C10a02.
Jing, F. et al., "Phylogenetic and experimental characterization of an acyl-ACP thioesterase family reveals significant diversity in enzymatic specificity and activity," BMC Biochemistry 2011, 12:44 (16 pages), BioMed Central, London, England.
Mayer, KM et al., "Identification of amino acid residues involved in substrate specificity of plant acyl-ACP thioesterases using a bioinformatics-guided approach," BMC Plant Biology, 2007, 7:1 (11 pages), doi:10.1186/1471-2229-7-1, BioMed Central, London, England.
Li, J et al., "Tryptophan fluorescence of the lux-specific *Vibrio harveyi* acyl-ACP thioesterase and its tryptophan mutants: structural properties and ligand-induced conformational change," Biochemistry, Nov. 1998, 37(46): 16130-16138, American Chemical Society, Washington, DC.
Madoka, Y et al., "Chloroplast transformation with modified *accD* operon increases acetyl-CoA carboxylase and causes extension of leaf longevity and increase in seed yield in tobacco," Plant Cell Physiol, Dec. 2002; 43(12):1518-1525, Japanese Society of Plant Physiologists, Kyoto, Japan.
Zou, J et al., "Modification of seed oil content and acyl composition in the Brassicaceae by expression of a yeast *sn-2* acyltransferase gene," The Plant Cell, Jun. 1997; 9(6):909-923, American Society of Plant Physiologists, Rockville, MD.
Jako, C et al.,"Seed-specific over-expression of an *Arabidopsis* cDNA encoding a diacylglycerol acyltransferase enhances seed oil content and seed weight," Plant Physiol, Jun. 2001; 126(2):861-874, American Society of Plant Physiologists, Rockville, MD.
Voekler, TA et al.,"Alteration of the specificity and regulation of fatty acid synthesis of *Escherichia coli* by expression of a plant medium-chain acyl-acyl carrier protein thioesterase," J Bacteriol, Dec. 1994; 176(23):7320-7327, American Society for Microbiology, Washington, DC.

*Primary Examiner* — Nashaat Nashed
(74) *Attorney, Agent, or Firm* — Sterne, Kessler, Goldstein & Fox P.L.L.C.

(57) ABSTRACT

A method of producing a lipid, comprising steps of
  introducing a gene that encodes the following protein (a) or (b) into a host, and thereby obtaining a transformant, and collecting a lipid from the transformant:
(a) A protein comprising an amino acid sequence of the $112^{nd}$ to $414^{th}$ amino acids set forth in SEQ ID NO: 1 in which an amino acid corresponding to the $209^{th}$ amino acid set forth in SEQ ID NO: 1 is substituted from tryptophan to threonine, glutamic acid or alanine, and having thioesterase activity, and
(b) A protein comprising an amino acid sequence of the protein (a) in which one to several amino acids other than the amino acid corresponding to the $209^{th}$ amino acid set forth in SEQ ID NO: 1 are deleted, substituted, inserted or added, and having thioesterase activity.

18 Claims, No Drawings

SEQUENCE LISTING

```
<160> NUMBER OF SEQ ID NOS: 20

<210> SEQ ID NO 1
<211> LENGTH: 414
<212> TYPE: PRT
<213> ORGANISM: Cocos nucifera

<400> SEQUENCE: 1

Met Val Ala Ser Val Ala Ala Ser Ser Ser Phe Phe Pro Val Pro Ser
 1               5                  10                  15

Ser Ser Ser Ser Ala Ser Ala Lys Ala Ser Arg Gly Ile Pro Asp Gly
                20                  25                  30

Leu Asp Val Arg Gly Ile Val Ala Lys Pro Ala Ser Ser Ser Gly Trp
            35                  40                  45

Met Gln Ala Lys Ala Ser Ala Arg Ala Ile Pro Lys Ile Asp Asp Thr
        50                  55                  60

Lys Val Gly Leu Arg Thr Asp Val Glu Glu Asp Ala Ala Ser Thr Ala
 65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val
```

```
                  115                 120                 125
Gly Lys Met Val Lys Asn Gly Leu Val Tyr Arg Gln Asn Phe Ser Ile
        130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Val Ala Lys Met Leu Val His Val Glu Arg Tyr Pro
        195                 200                 205

Trp Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
                245                 250                 255

Thr Arg Arg Leu Ser Lys Leu Pro Glu Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Ser Ala Ala His Val Arg Arg Gly Leu
    290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                325                 330                 335

Gly Tyr Glu Val Ala Thr Met Ser Leu Glu Tyr Arg Arg Glu Cys Arg
            340                 345                 350

Met Asp Ser Val Val Gln Ser Leu Thr Ala Val Ser Ser Asp His Ala
        355                 360                 365

Asp Gly Ser Pro Ile Val Cys Gln His Leu Leu Arg Leu Glu Asp Gly
    370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
                405                 410

<210> SEQ ID NO 2
<211> LENGTH: 1245
<212> TYPE: DNA
<213> ORGANISM: Cocos nucifera

<400> SEQUENCE: 2
atggtcgcct ccgttgctgc ctcatcatct ttcttcccgg tcccatcttc ctcctcctcg      60
gcctcggcaa agcttcgag aggcatccca gatggtttgg atgtccgggg catcgtagcg     120
aagccggcat cttcttccgg gtggatgcag gccaaggcaa gcgcccgagc catcccaaaa     180
atcgacgaca ccaaggttgg cctgcgacc gacgtcgagg aggatgccgc ttcaacggcg     240
cggagaactt catataacca attgccggac tggagcatgc tgcttgccgc gatcaggacc     300
atcttttcgg ccgcggagaa gcaatggacc ctgctcgatt ccaagaagag gggggccgac     360
gcggtcgcag atgcctctgg ggtcgggaag atggtcaaga atggacttgt ttacaggcag     420
aattttctta ccggtcccta cgaaatcggg gttgataaac gtgcttcggt agaggcattg     480
```

```
atgaatcatt tccaggaaac gtcgcttaac cattgcaagt gtattggcct tatgcatggc    540
ggctttggtt gtacaccaga gatgactcga agaaatctga tatgggttgt tgccaaaatg    600
ctggttcatg tcgaacgtta tccttggtgg ggagacgtgg ttcaaataaa tacgtggatt    660
agttcatctg gaaagaatgg tatgggacgt gattggcatg ttcatgactg ccaaactggc    720
ctacctatta tgaggggtac cagtgtctgg gtcatgatgg ataaacacac gaggagactg    780
tctaaacttc ctgaagaagt tagagcagag ataaccccct tcttttcaga gcgtgatgct    840
gttttggacg ataacggcag aaaacttccc aagttcgatg atgattctgc agctcatgtt    900
cgaaggggct tgactcctcg ttggcatgat ttcgatgtaa atcagcatgt gaacaatgtc    960
aaatacgtcg gctggattct tgagagcgtt cctgtgtgga tgttggatgg ctacgaggtt    1020
gcaaccatga gtctggaata ccggagggag tgtaggatgg atagtgtggt gcagtctctc    1080
accgccgtct cttccgacca cgccgacggc tcccccatcg tgtgccagca tcttctgcgg    1140
ctcgaggatg ggactgagat tgtgaggggt caaacagaat ggaggcctaa gcagcaggct    1200
cgtgatcttg ggaacatggg tctgcaccca actgagagta aatga                   1245
```

<210> SEQ ID NO 3  
<211> LENGTH: 414  
<212> TYPE: PRT  
<213> ORGANISM: Cocos nucifera

<400> SEQUENCE: 3

```
Met Val Ala Ser Val Ala Ala Ser Ser Phe Phe Pro Val Pro Ser
1               5                   10                  15

Ser Ser Ser Ser Ala Ser Ala Lys Ala Ser Arg Gly Ile Pro Asp Gly
                20                  25                  30

Leu Asp Val Arg Gly Ile Val Ala Lys Pro Ala Ser Ser Gly Trp
            35                  40                  45

Met Gln Ala Lys Ala Ser Ala Arg Ala Ile Pro Lys Ile Asp Asp Thr
50                  55                  60

Lys Val Gly Leu Arg Thr Asp Val Glu Glu Asp Ala Ala Ser Thr Ala
65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val
        115                 120                 125

Gly Lys Met Val Lys Asn Gly Leu Val Tyr Arg Gln Asn Phe Ser Ile
    130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Val Ala Lys Met Leu Val His Val Glu Arg Tyr Pro
        195                 200                 205

Thr Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240
```

```
Leu Pro Ile Met Arg Gly Thr Ser Val Trp Val Met Asp Lys His
                245                 250                 255

Thr Arg Arg Leu Ser Lys Leu Pro Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Ser Ala Ala His Val Arg Arg Gly Leu
        290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                325                 330                 335

Gly Tyr Glu Val Ala Thr Met Ser Leu Glu Tyr Arg Arg Glu Cys Arg
                340                 345                 350

Met Asp Ser Val Val Gln Ser Leu Thr Ala Val Ser Ser Asp His Ala
            355                 360                 365

Asp Gly Ser Pro Ile Val Cys Gln His Leu Leu Arg Leu Glu Asp Gly
        370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
                405                 410

<210> SEQ ID NO 4
<211> LENGTH: 1245
<212> TYPE: DNA
<213> ORGANISM: Cocos nucifera

<400> SEQUENCE: 4
atggtcgcct ccgttgctgc ctcatcatct ttcttcccgg tcccatcttc ctcctcctcg    60
gcctcggcaa aagcttcgag aggcatccca gatggtttgg atgtccgggg catcgtagcg   120
aagccggcat cttcttccgg gtggatgcag gccaaggcaa gcgcccgagc catcccaaaa   180
atcgacgaca ccaaggttgg cctgcggacc gacgtcgagg aggatgccgc ttcaacggcg   240
cggagaactt catataacca attgccggac tggagcatgc tgcttgccgc gatcaggacc   300
atcttttcgg ccgcggagaa gcaatggacc ctgctcgatt ccaagaagag ggggccgac    360 gcggtcgcag atgcctctgg ggtcgggaag atggtcaaga atggacttgt ttacaggcag   420
aattttctta ccggtccta cgaaatcggg gttgataaac gtgcttcggt agaggcattg    480
atgaatcatt tccaggaaac gtcgcttaac cattgcaagt gtattggcct tatgcatggc   540
ggctttggtt gtacaccaga gatgactcga agaaatctga tatgggttgt tgccaaaatg   600
ctggttcatg tcgaacgtta tcctacctgg ggagacgtgg ttcaaataaa tacgtggatt   660
agttcatctg gaaagaatgg tatgggacgt gattggcatg ttcatgactg ccaaactggc   720
ctacctatta tgaggggtac cagtgtctgg gtcatgatgg ataaacacac gaggagactg   780
tctaaacttc ctgaagaagt tagagcagag ataaccccct tcttttcaga gcgtgatgct   840
gttttggacg ataacggcag aaaacttccc aagttcgatg atgattctgc agctcatgtt   900
cgaaggggct tgactcctcg ttggcatgat ttcgatgtaa atcagcatgt gaacaatgtc   960
aaatacgtcg gctggattct tgagagcgtt cctgtgtgga tgttggatgg ctacgaggtt  1020
gcaaccatga gtctggaata ccggagggag tgtaggatgg atagtgtggt gcagtctctc  1080
accgccgtct cttccgacca cgccgacggc tcccccatcg tgtgccagca tcttctgcgg  1140
```

```
ctcgaggatg ggactgagat tgtgaggggt caaacagaat ggaggcctaa gcagcaggct    1200
cgtgatcttg ggaacatggg tctgcaccca actgagagta aatga                   1245
```

<210> SEQ ID NO 5
<211> LENGTH: 414
<212> TYPE: PRT
<213> ORGANISM: Cocos nucifera

<400> SEQUENCE: 5

```
Met Val Ala Ser Val Ala Ala Ser Ser Ser Phe Phe Pro Val Pro Ser
1               5                   10                  15

Ser Ser Ser Ala Ser Ala Lys Ala Ser Arg Gly Ile Pro Asp Gly
            20                  25                  30

Leu Asp Val Arg Gly Ile Val Ala Lys Pro Ala Ser Ser Ser Gly Trp
            35                  40                  45

Met Gln Ala Lys Ala Ser Ala Arg Ala Ile Pro Lys Ile Asp Asp Thr
    50                  55                  60

Lys Val Gly Leu Arg Thr Asp Val Glu Glu Asp Ala Ala Ser Thr Ala
65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val
        115                 120                 125

Gly Lys Met Val Lys Asn Gly Leu Val Tyr Arg Gln Asn Phe Ser Ile
130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Ala Lys Met Leu Val His Val Glu Arg Tyr Pro
        195                 200                 205

Glu Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
                245                 250                 255

Thr Arg Arg Leu Ser Lys Leu Pro Glu Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Ser Ala Ala His Val Arg Arg Gly Leu
    290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                325                 330                 335

Gly Tyr Glu Val Ala Thr Met Ser Leu Glu Tyr Arg Arg Glu Cys Arg
            340                 345                 350
```

Met Asp Ser Val Val Gln Ser Leu Thr Ala Val Ser Ser Asp His Ala
            355                 360                 365

Asp Gly Ser Pro Ile Val Cys Gln His Leu Leu Arg Leu Glu Asp Gly
        370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
                405                 410

<210> SEQ ID NO 6
<211> LENGTH: 1245
<212> TYPE: DNA
<213> ORGANISM: Cocos nucifera

<400> SEQUENCE: 6
atggtcgcct ccgttgctgc ctcatcatct ttcttcccgg tcccatcttc ctcctcctcg     60
gcctcggcaa aagcttcgag aggcatccca gatggtttgg atgtccgggg catcgtagcg    120
aagccggcat cttcttccgg gtggatgcag gccaaggcaa gcgcccgagc catcccaaaa    180
atcgacgaca ccaaggttgg cctgcggacc gacgtcgagg aggatgccgc ttcaacggcg    240
cggagaactt catataacca attgccggac tggagcatgc tgcttgccgc gatcaggacc    300
atcttttcgg ccgcggagaa gcaatggacc ctgctcgatt ccaagaagag gggggccgac    360
gcggtcgcag atgcctctgg ggtcgggaag atggtcaaga atggacttgt ttacaggcag    420
aatttttcta tccggtccta cgaaatcggg gttgataaac gtgcttcggt agaggcattg    480
atgaatcatt tccaggaaac gtcgcttaac cattgcaagt gtattggcct tatgcatggc    540
ggctttggtt gtacaccaga gatgactcga agaaatctga tatgggttgt tgccaaaatg    600
ctggttcatg tcgaacgtta tcctgagtgg ggagacgtgg ttcaaataaa tacgtggatt    660
agttcatctg gaaagaatgg tatgggacgt gattggcatg ttcatgactg ccaaactggc    720
ctacctatta tgagggggtac cagtgtctgg gtcatgatgg ataaacacac gaggagactg    780
tctaaacttc ctgaagaagt tagagcagag ataaccccct tcttttcaga gcgtgatgct    840
gttttggacg ataacggcag aaaacttccc aagttcgatg atgattctgc agctcatgtt    900
cgaaggggct tgactcctcg ttggcatgat ttcgatgtaa atcagcatgt gaacaatgtc    960
aaatacgtcg gctggattct tgagagcgtt cctgtgtgga tgttggatgg ctacgaggtt   1020
gcaaccatga gtctggaata ccggagggag tgtaggatgg atagtgtggt gcagtctctc   1080
accgccgtct cttccgacca cgccgacggc tcccccatcg tgtgccagca tcttctgcgg   1140
ctcgaggatg ggactgagat tgtgaggggt caaacagaat ggaggcctaa gcagcaggct   1200
cgtgatcttg ggaacatggg tctgcaccca actgagagta atga                     1245

<210> SEQ ID NO 7
<211> LENGTH: 414
<212> TYPE: PRT
<213> ORGANISM: Cocos nucifera

<400> SEQUENCE: 7

Met Val Ala Ser Val Ala Ala Ser Ser Ser Phe Phe Pro Val Pro Ser
1               5                   10                  15

Ser Ser Ser Ser Ala Ser Ala Lys Ala Ser Arg Gly Ile Pro Asp Gly
                20                  25                  30

Leu Asp Val Arg Gly Ile Val Ala Lys Pro Ala Ser Ser Ser Gly Trp
            35                  40                  45

```
Met Gln Ala Lys Ala Ser Ala Arg Ala Ile Pro Lys Ile Asp Asp Thr
 50                  55                  60

Lys Val Gly Leu Arg Thr Asp Val Glu Asp Ala Ala Ser Thr Ala
 65              70                  75                  80

Arg Arg Thr Ser Tyr Asn Gln Leu Pro Asp Trp Ser Met Leu Leu Ala
                 85                  90                  95

Ala Ile Arg Thr Ile Phe Ser Ala Glu Lys Gln Trp Thr Leu Leu
             100                 105                 110

Asp Ser Lys Lys Arg Gly Ala Asp Ala Val Ala Asp Ser Gly Val
             115                 120                 125

Gly Lys Met Val Lys Asn Gly Leu Val Tyr Arg Gln Asn Phe Ser Ile
130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Val Ala Lys Met Leu Val His Val Glu Arg Tyr Pro
        195                 200                 205

Ala Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
                245                 250                 255

Thr Arg Arg Leu Ser Lys Leu Pro Glu Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Ser Ala Ala His Val Arg Arg Gly Leu
    290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                325                 330                 335

Gly Tyr Glu Val Ala Thr Met Ser Leu Glu Tyr Arg Arg Glu Cys Arg
            340                 345                 350

Met Asp Ser Val Val Gln Ser Leu Thr Ala Val Ser Ser Asp His Ala
        355                 360                 365

Asp Gly Ser Pro Ile Val Cys Gln His Leu Leu Arg Leu Glu Asp Gly
    370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
                405                 410
```

<210> SEQ ID NO 8
<211> LENGTH: 1245
<212> TYPE: DNA
<213> ORGANISM: Cocos nucifera

<400> SEQUENCE: 8
atggtcgcct ccgttgctgc ctcatcatct ttcttcccgg tcccatcttc ctcctcctcg     60

-continued

| | |
|---|---|
| gcctcggcaa aagcttcgag aggcatccca gatggtttgg atgtccgggg catcgtagcg | 120 |
| aagccggcat cttcttccgg gtggatgcag gccaaggcaa gcgcccgagc catcccaaaa | 180 |
| atcgacgaca ccaaggttgg cctgcggacc gacgtcgagg aggatgccgc ttcaacggcg | 240 |
| cggagaactt catataacca attgccggac tggagcatgc tgcttgccgc gatcaggacc | 300 |
| atcttttcgg ccgcggagaa gcaatggacc ctgctcgatt ccaagaagag ggggggccgac | 360 |
| gcggtcgcag atgcctctgg ggtcgggaag atggtcaaga atggacttgt ttacaggcag | 420 |
| aattttcta tccggtccta cgaaatcggg gttgataaac gtgcttcggt agaggcattg | 480 |
| atgaatcatt tccaggaaac gtcgcttaac cattgcaagt gtattggcct tatgcatggc | 540 |
| ggctttggtt gtacaccaga gatgactcga agaaatctga tatgggttgt tgccaaaatg | 600 |
| ctggttcatg tcgaacgtta tcctgcctgg ggagacgtgg ttcaaataaa tacgtggatt | 660 |
| agttcatctg gaaagaatgg tatgggacgt gattggcatg ttcatgactg ccaaactggc | 720 |
| ctacctatta tgagggggtac cagtgtctgg gtcatgatgg ataaacacac gaggagactg | 780 |
| tctaaacttc ctgaagaagt tagagcagag ataaccccctt tcttttcaga gcgtgatgct | 840 |
| gttttggacg ataacggcag aaaacttccc aagttcgatg atgattctgc agctcatgtt | 900 |
| cgaagggct tgactcctcg ttggcatgat ttcgatgtaa atcagcatgt gaacaatgtc | 960 |
| aaatacgtcg gctggattct tgagagcgtt cctgtgtgga tgttggatgg ctacgaggtt | 1020 |
| gcaaccatga gtctggaata ccggagggag tgtaggatgg atagtgtggt gcagtctctc | 1080 |
| accgccgtct cttccgacca cgccgacggc tcccccatcg tgtgccagca tcttctgcgg | 1140 |
| ctcgaggatg ggactgagat tgtgaggggt caaacagaat ggaggcctaa gcagcaggct | 1200 |
| cgtgatcttg gaacatgggt tctgcaccca actgagagta aatga | 1245 |

<210> SEQ ID NO 9
<211> LENGTH: 39
<212> TYPE: DNA
<213> ORGANISM: Artificial Sequence
<220> FEATURE:
<223> OTHER INFORMATION: primer CTE FW

<400> SEQUENCE: 9
caggtcgact ctagagctcg attccaagaa gagggggggc                39

<210> SEQ ID NO 10
<211> LENGTH: 33
<212> TYPE: DNA
<213> ORGANISM: Artificial Sequence
<220> FEATURE:
<223> OTHER INFORMATION: primer CTE RV

<400> SEQUENCE: 10
ggtacccggg gatcctcatt tactctcagt tgg                33

<210> SEQ ID NO 11
<211> LENGTH: 25
<212> TYPE: DNA
<213> ORGANISM: Artificial Sequence
<220> FEATURE:
<223> OTHER INFORMATION: primer pMW219 FW

<400> SEQUENCE: 11
ctctagattg gtccactgct tctca                25

<210> SEQ ID NO 12
<211> LENGTH: 23

```
<212> TYPE: DNA
<213> ORGANISM: Artificial Sequence
<220> FEATURE:
<223> OTHER INFORMATION: primer pMW219 RV

<400> SEQUENCE: 12
gcggccgcgg catatggtgt gta                                           23

<210> SEQ ID NO 13
<211> LENGTH: 29
<212> TYPE: DNA
<213> ORGANISM: Artificial Sequence
<220> FEATURE:
<223> OTHER INFORMATION: primer CTE_W209T FW

<400> SEQUENCE: 13
acgttatcct acctggggag acgtggttc                                     29

<210> SEQ ID NO 14
<211> LENGTH: 29
<212> TYPE: DNA
<213> ORGANISM: Artificial Sequence
<220> FEATURE:
<223> OTHER INFORMATION: primer CTE_W209T RV

<400> SEQUENCE: 14
acgtctcccc aggtaggata acgttcgac                                     29

<210> SEQ ID NO 15
<211> LENGTH: 29
<212> TYPE: DNA
<213> ORGANISM: Artificial Sequence
<220> FEATURE:
<223> OTHER INFORMATION: primer CTE_W209E FW

<400> SEQUENCE: 15
acgttatcct gagtggggag acgtggttc                                     29

<210> SEQ ID NO 16
<211> LENGTH: 29
<212> TYPE: DNA
<213> ORGANISM: Artificial Sequence
<220> FEATURE:
<223> OTHER INFORMATION: primer CTE_W209E RV

<400> SEQUENCE: 16
acgtctcccc actcaggata acgttcgac                                     29

<210> SEQ ID NO 17
<211> LENGTH: 29
<212> TYPE: DNA
<213> ORGANISM: Artificial Sequence
<220> FEATURE:
<223> OTHER INFORMATION: primer CTE_W209A FW

<400> SEQUENCE: 17
acgttatcct gcctggggag acgtggttc                                     29

<210> SEQ ID NO 18
<211> LENGTH: 29
<212> TYPE: DNA
<213> ORGANISM: Artificial Sequence
<220> FEATURE:
<223> OTHER INFORMATION: primer CTE_W209A RV

<400> SEQUENCE: 18
```

```
acgtctcccc aggcaggata acgttcgac                                    29

<210> SEQ ID NO 19
<211> LENGTH: 29
<212> TYPE: DNA
<213> ORGANISM: Artificial Sequence
<220> FEATURE:
<223> OTHER INFORMATION: primer CTE_W209D FW

<400> SEQUENCE: 19
acgttatcct gactggggag acgtggttc                                    29

<210> SEQ ID NO 20
<211> LENGTH: 29
<212> TYPE: DNA
<213> ORGANISM: Artificial Sequence
<220> FEATURE:
<223> OTHER INFORMATION: primer CTE_W209D RV

<400> SEQUENCE: 20
acgtctcccc agtcaggata acgttcgac                                    29
```

METHOD OF PRODUCING LIPIDS USING A THIOESTERASE VARIANT

TECHNICAL FIELD

The present invention relates to a thioesterase variant and a method of producing lipids using the thioesterase variant.

BACKGROUND ART

Fatty acids are one of the principal components of lipids. In vivo, fatty acids are attached to glycerin via an ester bond to form lipids such as triacylglycerol. Many animals and plants store and utilize fatty acids as an energy source and these fatty acids and lipids are widely utilized for food or industrial use, for example, intermediate materials of foods, such as monoacylglycerol and diacylglycerol, and additives or intermediate materials for various industrial products. Further, higher alcohol derivatives that are obtained by reducing higher fatty acids having approximately 12 to 18 carbon atoms are used as surfactants. For example, alkyl sulfuric acid ester salts and alkylbenzenesulfonic acid salts are utilized as anionic surfactants, and polyoxyalkylene alkyl ethers and alkyl polyglycosides are utilized as nonionic surfactants, and these surfactants are used for detergents or disinfectants. Likewise, as other higher alcohol derivatives, alkylamine salts and mono- or dialkyl quaternary amine salts are commonly used for fiber treatment agents, hair conditioning agents or disinfectants, and benzalkonium type quaternary ammonium salts are commonly used for disinfectants or antiseptics. Furthermore, higher alcohols having approximately 18 carbon atoms are also useful as growth promoting agents for plants.

Fatty acids are widely used for various applications shown above, and therefore, it has been attempted to enhance the productivity of fatty acids or lipids in vivo by using animals and plants. For example, methods of increasing the lipid content in seeds by introducing acetyl-CoA carboxylase (ACCase) (Patent Literature 1, Non-Patent Literature 1, and Patent Literature 5); methods of increasing the lipid content in seeds by introducing a yeast sn-2 acyltransferase (SLC1-1) (Patent Literature 2, Patent Literature 3 and Non-Patent Literature 2); and methods of increasing the lipid content in seeds by introducing diacylglycerol acyltransferase gene (DGAT) (Patent Literature 4 and Non-Patent Literature 3), have been proposed. Further, several enzymes participating in the fatty acid biosynthesis are known, for example, a *Elaeis quineensis*-derived Acyl-ACP thioesterase (Patent Literature 6), a *Cocos nucifera* L.-derived Acyl-ACP thioesterase (Patent Literature 7), and a thioesterase having an amino acid sequence which is partially changed from that of an Acyl-ACP thioesterase derived from *Umbellularia californica* (Patent Literature 8).

CITATION LIST

Patent Literatures

Patent Literature 1: JP-A-2002-335786 ("JP-A" means unexamined published Japanese patent application)
Patent Literature 2: JP-A-11-506323
Patent Literature 3: WO 2008/076377 pamphlet
Patent Literature 4: WO 2000/036114 pamphlet
Patent Literature 5: U.S. Pat. No. 5,925,805
Patent Literature 6: JP-A-8-205863
Patent Literature 7: JP-A-2011-250781
Patent Literature 8: JP-A-2011-147438

Non-Patent Literatures

Non-Patent Literature 1: Madoka Y, Tomizawa K, Mizoi J, Nishida I, Nagano Y, Sasaki Y., "Chloroplast transformation with modified accD operon increases acetyl-CoA carboxylase and causes extension of leaf longevity and increase in seed yield in tobacco", Plant Cell Physiol., 2002 December, 43 (12), p. 1518-1525

Non-Patent Literature 2: Zou J, Katavic V, Giblin E M, Barton D L, MacKenzie S L, Keller W A, Hu X, Taylor D C., "Modification of seed oil content and acyl composition in the brassicaceae by expression of a yeast sn-2 acyltransferase gene", Plant Cell, 1997 June, 9 (6), p. 909-923

Non-Patent Literature 3: Jako C, Kumar A, Wei Y, Zou J, Barton D L, Giblin E M, Covello P S, Taylor D C., "Seed-specific over-expression of an *Arabidopsis* cDNA encoding a diacylglycerol acyltransferase enhances seed oil content and seed weight", Plant Physiol., 2001, 126 (2), p. 861-874

SUMMARY OF INVENTION

The present invention is contemplated for providing a thioesterase variant obtained by modifying an amino acid sequence of a wild-type thioesterase, and a method of producing a lipid using the thioesterase variant. The present invention is also contemplated for providing a transformant introduced with the thioesterase variant and having an enhanced ability to produce a lipid.

The present inventors made extensive studies so as to enhance the lipid productivity in animals and plants. As a result, the inventors attempted to partially modify an amino acid sequence of a thioesterase derived from *Cocos nucifera*, and they found that a transformant introduced with the thioesterase variant significantly enhances the productivity of lipids, as compared with a transformant introduced with the wild-type thioesterase. The present invention was completed based on this finding.

The present invention relates to a method of producing a lipid, comprising steps of
  introducing a gene that encodes the following protein (a) or (b) into a host, and thereby obtaining a transformant, and
  collecting a lipid from the transformant:
  (a) A protein comprising an amino acid sequence of the $112^{nd}$ to $414^{th}$ amino acids set forth in SEQ ID NO: 1 in which an amino acid corresponding to the $209^{th}$ amino acid set forth in SEQ ID NO: 1 is substituted from tryptophan to threonine, glutamic acid or alanine, and having thioesterase activity, and
  (b) A protein comprising an amino acid sequence of the protein (a) in which one to several amino acids other than the amino acid corresponding to the $209^{th}$ amino acid set forth in SEQ ID NO: 1 are deleted, substituted, inserted or added, and having thioesterase activity.
(Hereinafter, referred to as "the production method of the present invention")

The present invention also relates to a method of enhancing productivity of a lipid, comprising a step of
  introducing a gene that encodes the above protein (a) or (b) into a host, and thereby obtaining a transformant.

The present invention also relates to a transformant obtained by introducing a gene that encodes the above protein (a) or (b) into a host.
(Hereinafter, referred to as "the transformant of the present invention")

The present invention also relates to a protein of the above (a) or (b).
(Hereinafter, referred to as "the thioesterase variant of the present invention")

The present invention provides a transformant having an enhanced ability to produce lipids, compared to a transformant introduced with a wild-type thioesterase. The present invention also provides a production method using the transformant with excellent productivity of lipid. The thioesterase variant, the transformant and the production method of the present invention can be preferably used for the industrial production of fatty acids and lipids.

Other and further features and advantages of the invention will appear more fully from the following description.

MODE FOR CARRYING OUT THE INVENTION

Hereinafter, the thioesterase variant of the present invention, the transformant, and the method of producing a lipid using the thioesterase variant will be explained.

In the present invention, the term "lipid(s)" covers simple lipids such as neutral lipids, wax, ceramides; complex lipids such as phospholipids, glycolipids, sulfolipids; and derived lipids such as fatty acids, alcohols, hydrocarbons.

1. Thioesterase Variant

The thioesterase variant of the present invention is a protein having an amino acid sequence which is partially changed from an amino acid sequence of a wild-type thioesterase derived from *Cocos nucifera* set forth in SEQ ID NO: 1 (hereinafter, may be simply called the wild-type thioesterase, and is abbreviated to CTE), and having thioesterase activity.

The thioesterase is an acyl-acyl carrier protein (Acyl-ACP) thioesterase. Acyl-ACP thioesterases are enzymes involved in the triglyceride biosynthesis pathway and hydrolyzing a thioester bond of an acyl-acyl carrier protein to form free fatty acids. An acyl-acyl carrier protein is a composite composed of an acyl group as a fatty acid residue and an acyl carrier protein, and is an intermediate in the process of fatty acid biosynthesis in chloroplasts or plastids. Acyl-ACP thioesterases catalyze the fatty acid synthesis on an acyl carrier protein to generate free fatty acids, and then the free fatty acids are transported from plastids and supplied to the triglyceride synthesis. To date, several Acyl-ACP thioesterases having different reaction specificities depending on the kind of fatty acid residue of acyl-acyl carrier proteins are identified, and therefore, they are considered an important factor in determining fatty acid composition of an organism.

The thioesterase variant of the present invention includes the following protein (a) or (b):

(a) A protein comprising an amino acid sequence of the $112^{nd}$ to $414^{th}$ amino acids set forth in SEQ ID NO: 1 in which an amino acid corresponding to the $209^{th}$ amino acid set forth in SEQ ID NO: 1 is substituted from tryptophan to threonine, glutamic acid or alanine, and having thioesterase activity, and (b) A protein comprising an amino acid sequence of the protein (a) in which one to several amino acids other than the amino acid corresponding to the $209^{th}$ amino acid set forth in SEQ ID NO: 1 are deleted, substituted, inserted or added, and having thioesterase activity.

The protein (a) at least has an amino acid sequence of the $112^{nd}$ to $414^{th}$ amino acids in the wild-type thioesterase set forth in SEQ ID NO: 1. In the amino acid sequence of the wild-type thioesterase set forth in SEQ ID NO: 1, a region from the $112^{nd}$ amino acid to $414^{th}$ amino acid is considered particularly important for a thioesterase function, and necessary and sufficient for a protein to exhibit thioesterase activity (see Voelker, T. A., A. C. Worrell, L. Anderson, J. Bleibaum, C. Fan, D. H. Hawkins, S. E. Radke, and H. M. Davies, "Fatty acid biosynthesis redirected to medium chains in transgenic oilseed plants," Science, 1992, 257, p. 72-74). The protein (a) has the region necessary and sufficient for thioesterase activity, and acts thioesterase as demonstrated by the working example below.

Further, in the protein (a), the $209^{th}$ amino acid in the $112^{nd}$ to $414^{th}$ amino acid sequence set forth in SEQ ID NO: 1 is substituted from tryptophan (Trp; W) to any one of threonine (Thr; T), glutamic acid (Glu; E) and alanine (Ala; A).

Hereinafter, a thioesterase variant that an amino acid corresponding to the $209^{th}$ amino acid of SEQ ID NO: 1 is substituted to threonine will be abbreviated to CTE(W209T), a thioesterase variant that an amino acid corresponding to the $209^{th}$ amino acid of SEQ ID NO: 1 is substituted to glutamic acid will be abbreviated to CTE(W209E), and a thioesterase variant that an amino acid corresponding to the $209^{th}$ amino acid of SEQ ID NO: 1 is substituted to alanine will be abbreviated to CTE(W209A).

The protein (b) has an amino acid sequence having mutation of deletion, substitution, insertion or addition partially in the amino acid sequence of the protein (a), and has the thioesterase activity. However, the amino acid has the mutation of deletion, substitution, insertion or addition in a region other than the amino acid corresponding to the $209^{th}$ amino acid of SEQ ID NO: 1 as subjected to substitution in the protein (a). More specifically, the amino acid sequence of the protein (b) is based on the amino acid sequence of the $112^{th}$ to $414^{th}$ amino acids of SEQ ID NO: 1, in which the amino acid corresponding to the $209^{th}$ amino acid of SEQ ID NO: 1 in the sequence is substituted from tryptophan to any one of amino acids selected from threonine, glutamic acid and alanine, and one to several amino acids other than the amino acid corresponding to the $209^{th}$ amino acid subjected to substitution in the sequence are deleted, substituted, inserted or added.

In general, an amino acid sequence encoding an enzyme protein is not necessarily conserved over its entire length in order for the protein to exhibit enzymic activity, that is, a protein sequence includes a region that mutation of an amino acid sequence has little or no effect on its enzymic activity. In such a region that is not essential to the enzymic activity, the enzymic activity can be maintained even if some variations (mutations) such as deletions, substitutions, insertions or additions are introduced into amino acids of the region. Likewise, the present invention can be used the thioesterase variants having amino acid sequences which are partially changed from the sequence set forth in SEQ ID NO: 1 by deletion and the like, and which maintain the thioesterase activity.

The thioesterase activity of the variant protein can be confirmed by in-vitro activity measurement methods using Acyl-ACPs as substrates, such as a method described in Robert M et al. Plant Cell Physiol. 40(2): 155-163 (1999).

In the protein (b), one to several amino acids is preferably 1 to 10 amino acids, more preferably 1 to 5 amino acids, and particularly preferably 1 to 2 amino acids, in view of enhancing ability to produce lipids.

The protein (a) and the protein (b) may have other amino acid sequences in addition to the amino acid sequence corresponding to the amino acid sequence of the $112^{th}$ to $414^{th}$ amino acids of SEQ ID NO: 1. From a viewpoint of enhancing ability to produce lipids, other amino acid sequences preferably include the amino acid sequence of the $1^{st}$ to $111^{th}$ amino acids of SEQ ID NO: 1 or part of the sequences.

From the viewpoint of enhancing the ability to produce lipids, the protein (a) and the protein (b) preferably include the following protein (c) and protein (d).

(c) A protein consisting of an amino acid sequence set forth in SEQ ID NO: 1 in which the 209$^{th}$ amino acid is substituted from tryptophan to threonine, glutamic acid or alanine, and having thioesterase activity.

(d) A protein consisting of an amino acid sequence of the protein (c) in which one to several amino acids other than the 209$^{th}$ amino acid are deleted, substituted, inserted or added, and having thioesterase activity.

The protein (c) has an amino acid sequence in which the tryptophan corresponding to the 209$^{th}$ amino acid in the wild-type thioesterase set forth in SEQ ID NO: 1 is substituted to an amino acid selected from threonine, glutamic acid and alanine. An amino acid sequence of a thioesterase variant in which the 209$^{th}$ amino acid is substituted to threonine is set forth in SEQ ID NO: 3, an amino acid sequence of a thioesterase variant in which the 209$^{th}$ amino acid is substituted to glutamic acid is set forth in SEQ ID NO: 5, and an amino acid sequence of a thioesterase variant in which the 209$^{th}$ amino acid is substituted to alanine is set forth in SEQ ID NO: 7, respectively.

The protein (d) has an amino acid sequence in which the tryptophan corresponding to the 209$^{th}$ amino acid in the wild-type thioesterase set forth in SEQ ID NO: 1 is substituted to an amino acid selected from threonine, glutamic acid and alanine, and one to several amino acids other than the 209$^{th}$ amino acid are deleted, substituted, inserted or added, and has the thioesterase activity.

In the protein (d), one to several amino acids is preferably 1 to 10 amino acids, more preferably 1 to 5 amino acids, and particularly preferably 1 to 2 amino acids, in view of enhancing ability to produce lipids.

2. Gene Encoding Thioesterase Variant

Examples of genes encoding the protein (a) to (d) include the following genes (e) to (h), but the present invention is not limited thereto.

(e) A gene comprising a nucleotide sequence of the 334$^{th}$ to 1245$^{th}$ nucleotides set forth in SEQ ID NO: 2 in which nucleotides corresponding to the 625$^{th}$ to 627$^{th}$ nucleotides set forth in SEQ ID NO: 2 are substituted from nucleotides encoding tryptophan to nucleotides encoding threonine, glutamic acid or alanine, and encoding a protein having thioesterase activity.

(f) A gene comprising a nucleotide sequence of the gene (e) in which one to several nucleotides other than the nucleotides corresponding to the 625$^{th}$ to 627$^{th}$ nucleotides set forth in SEQ ID NO: 2 are deleted, substituted, inserted or added, and encoding a protein having thioesterase activity.

(g) A gene consisting of a nucleotide sequence set forth in SEQ ID NO: 2 in which the 625$^{th}$ to 627$^{th}$ nucleotides are substituted from nucleotides encoding tryptophan to nucleotides encoding threonine, glutamic acid or alanine, and encoding a protein having thioesterase activity.

(h) A gene consisting of a nucleotide sequence of the gene (g) in which one to several nucleotides other than the 625$^{th}$ to 627$^{th}$ nucleotides are deleted, substituted, inserted or added, and encoding a protein having thioesterase activity.

The nucleotide sequence set forth in SEQ ID NO: 2 is an example of the nucleotide sequence encoding the wild-type thioesterase derived from *Cocos nucifera*.

In the nucleotide sequence of the gene (f) or (h), one to several nucleotides is preferably 1 to 10 nucleotides, more preferably 1 to 5 nucleotides, and particularly preferably 1 to 2 nucleotides, in view of enhancing ability to produce lipids.

As the nucleotide sequence of the gene (g), one example of a nucleotide sequence in which nucleotides encoding tryptophan is substituted to nucleotides encoding threonine is set forth in SEQ ID NO: 4, one example of a nucleotide sequence in which nucleotides encoding tryptophan is substituted to nucleotides encoding glutamic acid is set forth in SEQ ID NO: 6, and one example of a nucleotide sequence in which nucleotides encoding tryptophan is substituted to nucleotides encoding alanine is set forth in SEQ ID NO: 8, respectively.

The thioesterase variant and the gene encoding the thioesterase variant can be obtained by conventional genetic engineering techniques. For example, the variant can be obtained based on amino acid or nucleotide sequence data of the wild-type thioesterase, and by introducing mutation such as substitution to the sequence at a desired position according to a site-specific mutagenesis method and the like.

The amino acid sequence of the wild-type thioesterase (SEQ ID NO: 1) and the nucleotide sequence encoding the amino acid sequence (for example, SEQ ID NO: 2) can be obtained from databases such as GenBank (for example, according to GenBank, protein sequence: AEM72521.1, mRNA sequence: JF338905.1). Based on the sequence data thus obtained, a gene that encodes the wild-type thioesterase can be obtained by artificial gene synthesis. The artificial synthesis of a gene can be achieved by utilizing the services such as Invitrogen, Inc. Furthermore, a gene that encodes the wild-type thioesterase can also be obtained by cloning from *Cocos nucifera*, and the cloning can be carried out by, for example, the methods described in Molecular Cloning—A LABORATORY MANUAL THIRD EDITION [Joseph Sambrook, David W. Russell, Cold Spring Harbor Laboratory Press (2001)] and the like.

Examples of the method for introducing site-specific mutation include a method of utilizing the splicing overlap extension (SOE) PCR (Horton et al., Gene 77, 61-68, 1989) used in the Example section that will be described below; the ODA method (Hashimoto-Gotoh et al., Gene, 152, 271-276, 1995); and the Kunkel method (Kunkel, T. A., Proc. Natl. Acad. Sci. USA, 1985, 82, 488). Furthermore, commercially available kits such as the Site-Directed Mutagenesis System Mutan-SuperExpress Km kit (Takara Bio, Inc.), the Transformer TM Site-Directed Mutagenesis kit (Clonetech Laboratories, Inc.), and the KOD-Plus-Mutagenesis kit (Toyobo Co., Ltd.) can also be utilized. Among these, according to the present invention, it is preferable to carry out the introduction of site-specific mutation according to the Kunkel method due to its high efficiency.

The gene encoding the thioesterase variant used in the present invention can be prepared by, for example, the following procedure. First, a cloning of the wild-type thioesterase gene derived from *Cocos nucifera* (for example, the nucleotide sequence set forth in SEQ ID NO: 2) is carried out, and a nucleotide sequence of the gene is incorporated into a vector by the In-Fusion (registered trademark) HD Cloning Kit (Clonthech, Mountain View, Calif.). Subsequently, a DNA fragment is amplified, according to a PCR method, using the resultant vector DNA as a template, and using as a primer an oligonucleotide containing a nucleotide sequence encoding an amino acid sequence in which the 209$^{th}$ amino acid in the amino acid sequence set forth in SEQ ID NO: 1 is substituted from tryptophan to threonine, glutamic acid or alanine (for example, an oligonucleotide having a nucleotide sequence set forth in SEQ ID NO: 13 or 14). A preferred example of the reaction conditions for PCR as follows: a thermal denaturation reaction of making a double-stranded DNA into single strands is carried out at 94° C. for 30 seconds; an annealing reaction of hybridizing a primer pair with the single-stranded DNA is carried out at 55° C. for about 30 seconds; an elongation reaction of operating a DNA polymerase is carried out at 72° C. for about 70 seconds; and a process consisting of these three reactions as one cycle is carried out in 30 cycles.

The DNA amplified according to PCR is treated with a DpnI enzyme that specifically cleaves a methylated DNA. *Escherichia coli* is transformed using the resultant treated material, and the resultant product is selected in an antibiotic-containing agar plate medium. Plasmids are extracted from the transformed *Escherichia coli*, and thus a gene encoding the thioesterase variant having a target amino acid mutation can be obtained.

3. Transformant (Recombinant)

The transformant of the present invention is obtained by introducing a gene that encodes the above protein (a) or (b) into a host. The transformant exhibits a significantly enhanced ability to produce lipids, as compared with a transformant introduced with the wild-type thioesterase gene. The ability to produce fatty acids and lipids of the wild-type thioesterase or the thioesterase variant can be measured by the method used in the Examples.

The transformant of the present invention is obtained by introducing a gene that encodes the thioesterase variant into a host according to a conventional genetic engineering method. Specifically, the transformant can be produced by preparing a vector which is capable of expressing a gene that encodes the thioesterase variant in a host cell, introducing this vector into host cells, and thereby transforming the host cells.

The host for transformation is not particularly limited, and examples of the host include microorganisms, algae, plants or animals. Among these, microorganisms, algae and plants are preferable, microorganisms and algae are more preferable, and microorganisms are further preferable, from the viewpoints of production efficiency and the usability of lipids.

As microorganisms for the host, prokaryotes and eukaryotes can be used. Prokaryotes include microorganisms which belong to the genus *Escherichia* or microorganisms which belong to the genus *Bacillus*. Eukaryotes include yeast or filamentous fungi. Among them, from the viewpoint of the productivity of useful materials, *Escherichia coli, Bacillus subtilis, Rhodosporidium toruloides*, and *Mortierella* sp. are preferable, *Escherichia coli* and *Bacillus subtilis* are more preferable, and *Escherichia coli* is further preferable.

As plants, from the viewpoint of a lipid content of seeds, *Arabidopsis thaliana*, rapeseed, coconut, palm, cuphea, and jatropha are preferable, and *Arabidopsis thaliana* is more preferable.

As algae, from a viewpoint of establishment of a gene recombination technique, Cyanobacteria (*Synechocystis* sp.), *Chlamydomonas* and *Phaeodactylum* are preferable, and Cyanobacteria (*Synechocystis* sp.) is more preferable.

A vector for use as the expression vector may be any vector capable of introducing the gene encoding the thioesterase variant into a host, and expressing the gene in the host cells. For example, a vector which has expression regulation regions such as a promoter and a terminator in accordance with the type of the host to be used, and has a replication initiation point, a selection marker or the like, can be used. Furthermore, the vector may also be a vector which is capable of self-proliferation and self-replication outside the chromosome, such as a plasmid, or may also be a vector which is incorporated into the chromosome.

Specific examples of the vector include, in the case of using a microorganism as the host, pBluescript II SK(−) (manufactured by Stratagene Corp.), pUC-based vector (manufactured by Takara Shuzo Co., Ltd.), a pET-based vector (manufactured by Takara Bio, Inc.), a pGEX-based vector (manufactured by GE Healthcare, Inc.), a pCold-based vector (manufactured by Takara Bio, Inc.), pHY300PLK (manufactured by Takara Bio, Inc.), pUB110 (Mckenzie, T. et al., (1986), Plasmid 15(2); p. 93-103), pBR322 (manufactured by Takara Bio, Inc.), pRS403 (manufactured by Stratagene Corp.), and pMW218/219 (manufactured by Nippon Gene Co., Ltd.). In the case of using a plant cell as the host, examples of the vector include a pRI-based vector (manufactured by Takara Bio, Inc.), a pBI-based vector (manufactured by Clontech Laboratories, Inc.), and an IN3-based vector (manufactured by Inplanta Innovations, Inc.). In the case of using an alga as the host, examples of the vector include pUC-based vector (manufactured by Takara Shuzo Co., Ltd.), a pET-based vector (manufactured by Takara Bio, Inc.), and pBluescript II SK(−) (manufactured by Stratagene Corp.).

Particularly, in the case of using Escherichia coli as the host, pBluescript II SK(−) and pMW218/219 are used preferably. In the case of using *Arabidopsis thaliana* as the host, a pRI-based vector and a pBI-based vector are used preferably. In the case of using Cyanobacteria as the host, pUC-based vector is used preferably.

The expression regulation regions such as a promoter and a terminator, and the selection marker are not particularly limited, and can be appropriately selected from conventionally used promoters, markers and the like in accordance with the type of the host to be used.

Specific examples of the promoter include lac promoter, trp promoter, tac promoter, trc promoter, T7 promoter, SpoVG promoter, cauliflower mosaic virus 35S RNA promoter, promoters for housekeeping genes such as actin and ubiquitin, rapeseed-derived *Napin* gene promoter, and plant-derived Rubisco promoter.

Examples of the selection marker include drug resistance genes such as antibiotic resistance genes (ampicillin resistance gene, chloramphenicol resistance gene, erythromycin resistance gene, neomycin resistance gene, kanamycin resistance gene, spectinomycin resistance gene, tetracycline resistance gene, blasticidin S resistance gene, bialaphos resistance gene, and hygromycin resistance gene). Further, it is also possible to use a deletion of an auxotrophy-related gene or the like as a selection marker.

A vector for transformation can be constructed by introducing the thioesterase variant into the above-described vector according to a conventional technique such as restriction enzyme treatment or ligation. The thioesterase variant can be obtained by the method described above.

The method for transformation is not particularly limited as long as it is a method capable of introducing a target gene into a host. For example, a method of using calcium ion, a general competent cell transformation method (J. Bacterial. 93, 1925 (1967)), a protoplast transformation method (Mol. Gen. Genet. 168, 111 (1979)), an electroporation method (FEMS Microbiol. Lett. 55, 135 (1990)), an LP transformation method (T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p.823-829) and the like, can be used.

Further, the selection of a transformant having a target gene fragment introduced therein can be carried out by using a selection marker or the like. For example, the selection can be carried out by using an indicator whether a transformant acquires the drug resistance as a result of introducing a vector-derived drug resistance gene into a host cell together with a target DNA fragment. Further, the introduction of a target DNA fragment can also be confirmed by PCR using a genome as a template.

4. Method of Producing Lipid

The transformant obtained as described above is used for production of a lipid.

The production method of the present invention comprises a step of collecting the lipid from the transformant into which the gene encoding the thioesterase variant is introduced. From a viewpoint of enhancing the productivity of lipids, the step preferably comprises a step of culturing or growing under appropriate conditions the transformant into which the gene encoding the thioesterase variant is introduced to obtain a culture or a growth product, and a step of collecting the lipid from the resultant culture or grown product. In the present specification, the culture includes a culture fluid and a transformant after culturing, and the grown product includes a transformant after growing.

The culture or growth conditions of the transformant can be selected in accordance with the type of the host into which the gene is introduced, and any appropriate preferred conditions can be employed. For instance, in the case of using *Escherichia coli* as the host for transformation, culture may be carried out in LB medium at 30° C. to 37° C. for half a day to 1 day. In the case of using *Arabidopsis thaliana* as the host for transformation, growth may be carried out under the temperature conditions of 20° C. to 25° C., by continuously irradiating white light or under the illumination conditions of a light period of 16 hours and a dark period of 8 hours, for one to two months. In the case of using Cyanobacteria as the host for transformation, culture may be carried out under the temperature conditions of 25° C. to 32° C., by continuously irradiating white light or under the illumination conditions of a light period of 12 hours and a dark period of 12 hours, for one week to one month.

From the viewpoint of the production efficiency of fatty acids and lipids, substrates for thioesterase or precursor substances participating in the fatty acid biosynthesis, such as glycerol, acetic acid, malonic acid and the like, may be added to the medium.

As the method of collecting lipids produced in the transformant, methods that are conventionally used to isolate lipid components and the like from organisms may be used. For example, lipid components can be isolated and collected from the culture, grown product or transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the culture, grown product or transformant through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

According to the production method of the present invention, the productivity of lipids can be significantly enhanced by using the thioesterase variant of the present invention in comparison with a case where the wild-type thioesterase is used.

In view of usability, lipids to be produced according to the production method of the present invention contains preferably at least one kind selected from a simple lipid and a derived liquid, further preferably, a derived lipid, and still further preferably, a fatty acid or an ester thereof. From usability for a surfactant or the like, the fatty acid or the ester thereof contained in the lipid is preferably a fatty acid having 12 to 16 carbon atoms or an ester thereof, further preferably, a fatty acid having 12 to 14 carbon atoms or an ester thereof, and still further preferably, a lauric acid or an ester thereof. These higher fatty acids can be reduced to generate higher alcohol derivatives, and the higher alcohol derivatives can be utilized for the surfactant.

From a viewpoint of utilizing the fatty acid as the surfactant, a content of the fatty acid having 12 to 16 carbon atoms in total collected lipid components is preferably 65% by mass or more, more preferably, 75% by mass or more, and further preferably, 85% by mass or more. Moreover, from the viewpoint of utilizing the fatty acid as the surfactant, a content of the fatty acid having 12 to 14 carbon atoms in the total collected lipid components is preferably 50% by mass or more, more preferably, 55% by mass or more, and further preferably, 60% by mass or more. Further, from the viewpoint of utilizing the lauric acid as the surfactant, a content of the lauric acid contained in the total collected lipid components is preferably 27% by mass or more, more preferably, 28% by mass or more, and further preferably, 30% by mass or more. Here, "total collected lipid components" means total lipid components calculated by the method applied in Examples.

The fatty acids or lipids obtained by the production method and the transformant of the present invention can be utilized for food, as well as can be utilized as an emulsifier incorporated into cosmetic products or the like, a cleansing agent such as a soap or a detergent, a fiber treatment agent, a hair conditioning agent, a disinfectant or an antiseptic.

With regard to the embodiments described above, also disclosed by the present invention includes a method, a transformant, a protein and a gene described below.

<1> A method of producing a lipid, comprising steps of introducing a gene that encodes the following protein (a) or (b) into a host, and thereby obtaining a transformant, and collecting a lipid from the transformant:

(a) A protein comprising an amino acid sequence of the $112^{nd}$ to $414^{th}$ amino acids set forth in SEQ ID NO: 1 in which an amino acid corresponding to the $209^{th}$ amino acid set forth in SEQ ID NO: 1 is substituted from tryptophan to threonine, glutamic acid or alanine, and having thioesterase activity, and (b) A protein comprising an amino acid sequence of the protein (a) in which one to several amino acids (preferably 1 to 10 amino acids, more preferably 1 to 5 amino acids, and particularly preferably 1 to 2 amino acids) other than the amino acid corresponding to the $209^{th}$ amino acid set forth in SEQ ID NO: 1 are deleted, substituted, inserted or added, and having thioesterase activity.

<2> The method according to <1>, wherein the protein (a) or (b) is the following protein (c) or (d):

(c) A protein consisting of an amino acid sequence set forth in SEQ ID NO: 1 in which the $209^{th}$ amino acid is substituted from tryptophan to threonine, glutamic acid or alanine, and having thioesterase activity, and (d) A protein consisting of an amino acid sequence of the protein (c) in which one to several amino acids (preferably 1 to 10 amino acids, more preferably 1 to 5 amino acids, and particularly preferably 1 to 2 amino acids) other than the $209^{th}$ amino acid are deleted, substituted, inserted or added, and having thioesterase activity.

<3> The method according to <1> or <2>, wherein the gene that encodes the protein is a gene selected from the following (e) to (h):

(e) A gene comprising a nucleotide sequence of the 334$^{th}$ to 1245$^{th}$ nucleotides set forth in SEQ ID NO: 2 in which nucleotides corresponding to the 625$^{th}$ to 627$^{th}$ nucleotides set forth in SEQ ID NO: 2 are substituted from nucleotides encoding tryptophan to nucleotides encoding threonine, glutamic acid or alanine, and encoding a protein having thioesterase activity, (f) A gene comprising a nucleotide sequence of the gene (e) in which one to several nucleotides (preferably 1 to 10 nucleotides, more preferably 1 to 5 nucleotides, and particularly preferably 1 to 2 nucleotides) other than the nucleotides corresponding to the 625$^{th}$ to 627$^{th}$ nucleotides set forth in SEQ ID NO: 2 are deleted, substituted, inserted or added, and encoding a protein having thioesterase activity, (g) A gene consisting of a nucleotide sequence set forth in SEQ ID NO: 2 in which the 625$^{th}$ to 627$^{th}$ nucleotides are substituted from nucleotides encoding tryptophan to nucleotides encoding threonine, glutamic acid or alanine, and encoding a protein having thioesterase activity, and (h) A gene consisting of a nucleotide sequence of the gene (g) in which one to several nucleotides (preferably 1 to 10 nucleotides, more preferably 1 to 5 nucleotides, and particularly preferably 1 to 2 nucleotides) other than the 625$^{th}$ to 627$^{th}$ nucleotides are deleted, substituted, inserted or added, and encoding a protein having thioesterase activity.

<4> The method according to any one of <1> to <3>, wherein the host is selected from plants, algae and microorganisms.

<5> The method according to any one of <1> to <4>, wherein the host is selected from *Arabidopsis thaliana*, Cyanobacteria and *Escherichia coli*.

<6> The method according to any one of <1> to <5>, wherein the lipid contains a lauric acid.

<7> The method according to any one of <1> to <6>, wherein the lipid contains a lauric acid in an amount of 27% by mass or more, preferably 28% by mass or more, and more preferably 30% by mass or more.

<8> The method according to any one of <1> to <7>, wherein the lipid contains fatty acids having 12 to 16 carbon atoms in an amount of 65% by mass or more, preferably 75% by mass or more, and more preferably 85% by mass or more.

<9> The method according to any one of <1> to <8>, wherein the host is a microorganism.

<10> The method according to any one of <1> to <9>, wherein the host is *Escherichia coli*.

<11> A method of enhancing productivity of a lipid, comprising a step of
introducing a gene that encodes the above protein (a) or (b) into a host, and thereby obtaining a transformant.

<12> A transformant obtained by introducing a gene that encodes the above protein (a) or (b) into a host.

<13> The transformant according to <12>, wherein the protein (a) or (b) is the above protein (c) or (d).

<14> The transformant according to <12> or <13>, wherein the gene that encodes the protein is a gene selected from the above (e) to (h).

<15> The transformant according to any one of <12> to <14>, wherein the host is selected from plants, algae and microorganisms.

<16> The transformant according to any one of <12> to <15>, wherein the host is selected from *Arabidopsis thaliana*, Cyanobacteria and *Escherichia coli*.

<17> The transformant according to any one of <12> to <16>, wherein the host is a microorganism.

<18> The transformant according to any one of <12> to <17>, wherein the host is *Escherichia coli*.

<19> A protein of the above (a) or (b).

<20> The protein according to <19>, which is the above protein (c) or (d).

<21> A gene selected from the above (e) to (h) that encode the protein according to <19> or <20>.

<22> Use of the transformant according to any one of <12> to <18> for the production of a lipid.

EXAMPLES

Hereinafter, the present invention will be described more in detail with reference to Examples, but the present invention is not limited thereto.

Example

1. Construction of Wild-Type Thioesterase (CTE) Gene Expression Plasmid

A DNA fragment of the wild-type thioesterase gene was amplified by PCR using a gene that encodes the wild-type thioesterase having the nucleotide sequence set forth in SEQ ID NO: 2 as a template, and using a pair of primers of CTE FW (SEQ ID NO: 9) and CTE RV (SEQ ID NO: 10) as shown in the following Table 1. Moreover, a linearly formed pMW 219 was obtained by using a plasmid vector pMW 219 (manufactured by Nippon Gene Co., LTD.) as a template, and according to PCR using a pair of primers of pMW 219 FW (SEQ ID NO: 11) and pMW 219 RV (SEQ ID NO: 12), and then the resultant product was subjected to DpnI treatment. These two DNA fragments were linked using an In-Fusion (registered trademark) HD Cloning Kit (Clonthech, Mountain View, Calif.) to construct a plasmid. The plasmid included a wild-type thioesterase gene fragment (nucleotide sequence of the 334$^{th}$ to 1245$^{th}$ nucleotides in the nucleotide sequence set forth in SEQ ID NO: 2) being fused to the 27$^{th}$ amino acid on an N-terminus of a vector-derived LacZ protein, and the plasmid can express the wild-type thioesterase gene. The insertion of the gene encoding the wild-type thioesterase into the plasmid was confirmed by DNA sequencing.

2. Construction of Thioesterase Variant Gene Expression Plasmid

DNA fragments including a gene encoding a thioesterase variant CTE(W209T), CTE(W209E), CTE(W209A), or CTE(W209D) were amplified according to PCR. In these variants, the nucleotide sequence TGG (tryptophan: W) at the position of 625$^{th}$ to 627$^{th}$ in the wild-type thioesterase sequence set forth in SEQ ID NO: 2, was substituted by ACC (threonine: T), GAG (glutamic acid: E), GCC (alanine: A), or GAC (aspartic acid: D). The PCR was carried out by using the wild-type thioesterase expression plasmid constructed in the above section 1 as a template, and a primer pair of CTE_W209T FW (SEQ ID NO: 13) and CTE_W209T RV (SEQ ID NO: 14), a primer pair of CTE_W209E FW (SEQ ID NO: 15) and CTE_W209E RV (SEQ ID NO: 16), a primer pair of CTE_W209A FW (SEQ ID NO: 17) and CTE_W209A RV (SEQ ID NO: 18), or a primer pair of CTE_W209D FW (SEQ ID NO: 19) and CTE_W209D RV (SEQ ID NO: 20) as shown in the following Table 1. The PCR reaction mixtures thus obtained were treated with Dpn I to digest the template DNA. *Escherichia coli* were transformed by each of the reaction mixture to construct plasmids for expression of the thioesterase variant. The insertion of the gene encoding the thioesterase variant into the plasmid was confirmed by DNA sequencing.

TABLE 1

| Primers | | |
|---|---|---|
| CTE FW | CAGGTCGACTCTAGAGCTCGATTCCAAGAAGAGGGGGGC | SEQ ID NO: 9 |
| CTE RV | GGTACCCGGGGATCCTCATTTACTCTCAGTTGG | SEQ ID NO: 10 |
| pMW219 FW | CTCTAGATTGGTCCACTGCTTCTCA | SEQ ID NO: 11 |
| pMW219 RV | GCGGCCGCGGCATATGGTGTGTA | SEQ ID NO: 12 |
| CTE_W209T FW | ACGTTATCCTACCTGGGGAGACGTGGTTC | SEQ ID NO: 13 |
| CTE_W209T RV | ACGTCTCCCCAGGTAGGATAACGTTCGAC | SEQ ID NO: 14 |
| CTE_W209E FW | ACGTTATCCTGAGTGGGGAGACGTGGTTC | SEQ ID NO: 15 |
| CTE_W209E RV | ACGTCTCCCCACTCAGGATAACGTTCGAC | SEQ ID NO: 16 |
| CTE_W209A FW | ACGTTATCCTGCCTGGGGAGACGTGGTTC | SEQ ID NO: 17 |
| CTE_W209A RV | ACGTCTCCCCAGGCAGGATAACGTTCGAC | SEQ ID NO: 18 |
| CTE_W209D FW | ACGTTATCCTGACTGGGGAGACGTGGTTC | SEQ ID NO: 19 |
| CTE_W209D RV | ACGTCTCCCCAGTCAGGATAACGTTCGAC | SEQ ID NO: 20 |

3. Construction of Transformant

An *Escherichia coli* mutant strain, strain K27 (fadD88) (Overath et al, Eur. J. Biochem. 7, 559-574, 1969), was transformed by a competent cell transformation method, using the plasmid that express the wild-type thioesterase or the plasmid that express the thioesterase variant constructed in the above. The transformed strain K27 was left to stand overnight at 30° C., and colonies thus obtained were inoculated in 1 mL of LBKm liquid medium (Bacto Trypton 1%, yeast extract 0.5%, NaCl 1%, and kanamycin 50 µg/mL), and was subjected to shaking culture for 12 hours at 30° C. After 12 hours, 20 µL of the culture fluid was added to another 2.0 mL of LBKm liquid medium, and the mixture was subjected to shaking culture at 30° C. After a lapse of 36 hours from the initiation of culture, lipid components contained in the culture fluid were analyzed by the method described below. Further, after a lapse of 36 hours from the initiation of culture, the light absorbance at 600 nm (OD600) of the culture fluid was measured to calculate the cell numbers of *Escherichia coli* contained in the culture fluid. As a negative control, *Escherichia coli* strain K27 that was transformed with plasmid vector pMW219, was also subjected to the same experiment.

4. Extraction of Lipid in *Escherichia coli* Culture Fluid and Analysis of Fatty Acid Contained Therein To 1 mL of the culture fluid obtained after a lapse of 36 hours from the initiation of culture, 10 µL of 2N hydrochloric acid, and 30 µL of 7-pentadecanone (5 mg/mL) dissolved in methanol as an internal standard were added. To this liquid, 0.5 mL of chloroform and 1 mL of methanol were added, and the mixture was sufficiently stirred and then was left to stand for 15 minutes. Further, 0.5 mL of a 1.5% aqueous solution of potassium chloride and 0.5 mL of chloroform were added thereto, and the mixture was sufficiently stirred and then was left to stand for 15 minutes. The mixture was centrifuged for 5 minutes at room temperature and at 1,500 rpm, and then the lower layer was collected and dried with nitrogen gas. 1 mL of a boron trifluoride-methanol complex solution was added to the dried sample, and the mixture was kept warm at 80° C. for 10 minutes to thereby performing methyl esterification treatment of fatty acids. Thereafter, 1 mL of saturated brine and 1 mL of hexane were added thereto, and the mixture was sufficiently stirred and then was left to stand for 30 minutes. The upper layer was collected and provided for gas chromatographic analysis (Agilent 6890). The gas chromatography was carried out under the conditions as follows: [capillary column: DB-1 MS 30 m×200 µm×0.25 µm (J&W Scientific, Inc.), mobile layer: high purity helium, flow rate inside the column: 1.0 mL/min, temperature rise program: 100° C. (for 1 min)→10° C./min→300° C. (for 5 min), equilibration time: for 1 min, injection port: split injection (split ratio: 100:1), pressure 14.49 psi, 104 mL/min, amount of injection 1 µL, vial cleaning: methanol•chloroform, detector temperature: 300° C.].

5. Analysis of Lipid and Fatty Acid Content in *Escherichia coli* Culture Fluid

Amounts of fatty acid methyl esters were quantitatively determined based on the peak areas of the waveform data obtained by the above gas chromatographic analysis. The peak areas corresponding to the individual fatty acids were compared with that of 7-pentadecanone as the internal standard, and carried out corrections between the samples, and then the contents of the individual fatty acids per liter of the culture fluid were calculated. Further, the contents of the individual fatty acids thus calculated were normalized with respect to the cell numbers of *Escherichia coli* contained in the culture fluid previously measured (OD600). Furthermore, the total content of the individual fatty acids (the total lipid content) was calculated by summing the contents of the individual fatty acids thus obtained. The results are shown in Table 2. Further, ratios of the contents of the individual fatty acids in the total content of the individual fatty acids were shown in Table 3. In addition, in Table 2, the contents of the individual fatty acids and the total content of the individual fatty acids (total lipid content) were expressed in terms of relative values when the content in the transformant into which the wild-type thioesterase gene was introduced was taken as 1.

TABLE 2

| | Fatty acid content | | | | | |
|---|---|---|---|---|---|---|
| | Lauric acid (C12:0) | Myristic acid (C14:0) | Palmitic acid (C16:0) | Palmitoleic acid (C16:1) | Stearic acid (C18:0) Oleic acid (C18:1) | Total content of fatty acids (Total lipid content) |
| pMW (Control) | 0 | 0.06 | 0.08 | 1.67 | 0.24 | 0.28 |
| CTE | 1.00 | 1.00 | 1.00 | 1.00 | 1.00 | 1.00 |
| CTE(W209T) | 2.14 | 1.63 | 1.08 | 1.76 | 1.04 | 1.64 |
| CTE(W209E) | 1.60 | 1.33 | 0.92 | 1.67 | 1.19 | 1.45 |
| CTE(W209A) | 1.47 | 1.27 | 0.95 | 1.42 | 0.85 | 1.25 |
| CTE(W209D) | 1.07 | 1.04 | 0.82 | 1.13 | 0.79 | 1.00 |

TABLE 3

| | Lauric acid (C12:0) | Myristic acid (C14:0) | Palmitic acid (C16:0) | Palmitoleic acid (C16:1) | Stearic acid (C18:0) Oleic acid (C18:1) | Total content of fatty acids (Total lipid content) |
|---|---|---|---|---|---|---|
| CTE | 25.0% | 35.4% | 14.8% | 13.1% | 11.7% | 100% |
| CTE(W209T) | 32.6% | 35.7% | 8.7% | 15.6% | 7.4% | 100% |
| CTE(W209E) | 29.0% | 34.2% | 8.8% | 18.0% | 10.0% | 100% |
| CTE(W209A) | 29.4% | 35.8% | 10.0% | 16.8% | 8.0% | 100% |
| CTE(W209D) | 26.6% | 36.8% | 10.7% | 16.7% | 9.2% | 100% |

As is apparent from Table 2, the transformants having the thioesterase variant CTE(W209T), CTE(W209E), or CTE(W209A) exhibited an increase in the contents (amounts of production) of the individual fatty acids and the total content of the individual fatty acids (the total lipid content) to a large extent, as compared with the transformant having the wild-type thioesterase gene.

In contrast, the transformant having the thioesterase variant CTE(W209D) exhibited almost the same production amount of the individual fatty acids as the transformant having the wild-type thioesterase gene.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2012-206972 filed in Japan on Sep. 20, 2012, which is entirely herein incorporated by reference.

What is claimed is:

1. A method of producing a lipid, comprising steps of introducing a gene that encodes the following protein (a) or (b) into a host, and thereby obtaining a transformant,
   culturing or growing the transformant to obtain a culture or grown product, and
   collecting a lipid from the culture media, grown product or transformant,
   wherein the proteins (a) and (b) are:
   (a) A protein comprising an amino acid sequence of the $112^{nd}$ to $414^{th}$ amino acids set forth in SEQ ID NO: 1 in which an amino acid corresponding to the $209^{th}$ amino acid set forth in SEQ ID NO: 1 is substituted from tryptophan to threonine, glutamic acid or alanine, and having thioesterase activity, and
   (b) A protein comprising an amino acid sequence of the protein (a) in which one to ten amino acids other than the amino acid corresponding to the $209^{th}$ amino acid set forth in SEQ ID NO: 1 are deleted, substituted, inserted or added, and having thioesterase activity.

2. The method according to claim 1, wherein the host is selected from plants, algae and microorganisms.

3. The method according to claim 1, wherein the host is selected from *Arabidopsis thaliana*, Cyanobacteria and *Escherichia coli*.

4. The method according to claim 1, wherein the lipid contains a lauric acid.

5. The method according to claim 1, wherein the lipid contains a lauric acid in an amount of 27% by mass or more.

6. The method according to claim 1, wherein the lipid contains fatty acids having 12 to 16 carbon atoms in an amount of 65% by mass or more.

7. The method according to claim 1, wherein the protein (a) or (b) is the following protein (c) or (d):
   (c) A protein consisting of an amino acid sequence set forth in SEQ ID NO: 1 in which the $209^{th}$ amino acid is substituted from tryptophan to threonine, glutamic acid or alanine, and having thioesterase activity, and
   (d) A protein consisting of an amino acid sequence of the protein (c) in which one to ten amino acids other than the $209^{th}$ amino acid are deleted, substituted, inserted or added, and having thioesterase activity.

8. The method according to claim 7, wherein the protein (c) consists of the amino acid sequence set forth in SEQ ID NO: 3, SEQ ID NO: 5, or SEQ ID NO: 7.

9. The method according to claim 1, wherein the gene that encodes the protein is a gene selected from the following (e) to (h):
   (e) A gene comprising a nucleotide sequence of the $334^{th}$ to $1245^{th}$ nucleotides set forth in SEQ ID NO: 2 in which nucleotides corresponding to the $625^{th}$ to $627^{th}$ nucleotides set forth in SEQ ID NO: 2 are substituted from nucleotides encoding tryptophan to nucleotides encoding threonine, glutamic acid or alanine, and encoding a protein having thioesterase activity,
   (f) A gene comprising a nucleotide sequence of the gene (e) in which one to ten nucleotides other than the nucleotides corresponding to the $625^{th}$ to $627^{th}$ nucleotides set forth in SEQ ID NO: 2 are deleted, substituted, inserted or added, and encoding a protein having thioesterase activity,
   (g) A gene consisting of a nucleotide sequence set forth in SEQ ID NO: 2 in which the $625^{th}$ to $627^{th}$ nucleotides are substituted from nucleotides encoding tryptophan to nucleotides encoding threonine, glutamic acid or alanine, and encoding a protein having thioesterase activity, and
   (h) A gene consisting of a nucleotide sequence of the gene (g) in which one to ten nucleotides other than the $625^{th}$ to $627^{th}$ nucleotides are deleted, substituted, inserted or added, and encoding a protein having thioesterase activity.

10. The method according to claim 9, wherein the gene (g) is consisting of the nucleotide sequence set forth in SEQ ID NO: 4, SEQ ID NO: 6, or SEQ ID NO: 8.

11. The method according to claim 1, wherein the lipid contains fatty acids having 12 to 16 carbon atoms in an amount of 65% by mass or more.

12. A transformant obtained by introducing a gene that encodes the following protein (a) or (b) into a host:
    (a) A protein comprising an amino acid sequence of the $112^{nd}$ to $414^{th}$ amino acids set forth in SEQ ID NO: 1 in which an amino acid corresponding to the $209^{th}$ amino acid set forth in SEQ ID NO: 1 is substituted from tryptophan to threonine, glutamic acid or alanine, and having thioesterase activity, and (b) A protein comprising an amino acid sequence of the protein (a) in which one to ten amino acids other than the amino acid corresponding to the 209$^{th}$ amino acid set forth in SEQ ID NO: 1 are deleted, substituted, inserted or added, and having thioesterase activity.

13. The transformant according to claim 12, wherein the host is selected from plants, algae and microorganisms.

14. The transformant according to claim 12, wherein the host is selected from the group consisting of *Arabidopsis thaliana*, Cyanobacteria and *Escherichia coli*.

15. The transformant according to claim 12, wherein the protein (a) or (b) is the following protein (c) or (d):

(c) A protein consisting of an amino acid sequence set forth in SEQ ID NO: 1 in which the 209$^{th}$ amino acid is substituted from tryptophan to threonine, glutamic acid or alanine, and having thioesterase activity, and (d) A protein consisting of an amino acid sequence of the protein (c) in which one to ten amino acids other than the 209$^{th}$ amino acid are deleted, substituted, inserted or added, and having thioesterase activity.

16. The transformant according to claim 15, wherein the protein (c) consists of the amino acid sequence set forth in SEQ ID NO: 3, SEQ ID NO: 5, or SEQ ID NO: 7.

17. The transformant according to claim 12, wherein the gene that encodes the protein is a gene selected from the following (e) to (h):

(e) A gene comprising a nucleotide sequence of the 334$^{th}$ to 1245$^{th}$ nucleotides set forth in SEQ ID NO: 2 in which nucleotides corresponding to the 625$^{th}$ to 627$^{th}$ nucleotides set forth in SEQ ID NO: 2 are substituted from nucleotides encoding tryptophan to nucleotides encoding threonine, glutamic acid or alanine, and encoding a protein having thioesterase activity, (f) A gene comprising a nucleotide sequence of the gene (e) in which one to ten nucleotides other than the nucleotides corresponding to the 625$^{th}$ to 627$^{th}$ nucleotides set forth in SEQ ID NO: 2 are deleted, substituted, inserted or added, and encoding a protein having thioesterase activity, (g) A gene consisting of a nucleotide sequence set forth in SEQ ID NO: 2 in which the 625$^{th}$ to 627$^{th}$ nucleotides are substituted from nucleotides encoding tryptophan to nucleotides encoding threonine, glutamic acid or alanine, and encoding a protein having thioesterase activity, and (h) A gene consisting of a nucleotide sequence of the gene (g) in which one to ten nucleotides other than the 625$^{th}$ to 627$^{th}$ nucleotides are deleted, substituted, inserted or added, and encoding a protein having thioesterase activity.

18. The transformant according to claim 17, wherein the gene (g) consists of the nucleotide sequence set forth in SEQ ID NO: 4, SEQ ID NO: 6, or SEQ ID NO: 8.

* * * * *